United States Patent
Ueland et al.

(10) Patent No.: US 6,911,415 B1
(45) Date of Patent: Jun. 28, 2005

(54) FUNGICIDAL COMPOSITIONS CONTAINING ORGANIC COMPOSITIONS DERIVED FROM NATURAL ORGANIC MATERIALS, PHOSPHOROUS ACID, PHOSPHITE SALTS AND PHOSPHATE SALTS, METHODS OF MAKING SAME AND METHODS OF APPLYING SAME TO PLANTS

(75) Inventors: Carl Ueland, Biola, CA (US); Dave Davis, Biola, CA (US); John R. Marihart, Biola, CA (US); Frank Shanahan, Biola, CA (US)

(73) Assignee: Actagro, LLC, Biola, CA (US)

( * ) Notice: Subject to any disclaimer, the term of this patent is extended or adjusted under 35 U.S.C. 154(b) by 0 days.

(21) Appl. No.: 10/166,231

(22) Filed: Jun. 6, 2002

Related U.S. Application Data

(60) Provisional application No. 60/296,928, filed on Jun. 9, 2001.

(51) Int. Cl.$^7$ .............................................. A01N 59/00
(52) U.S. Cl. ..................................................... 504/119
(58) Field of Search ........................... 504/119; 424/405

(56) References Cited

U.S. PATENT DOCUMENTS

| | | |
|---|---|---|
| 4,075,324 A | 2/1978 | Thizy et al. |
| 4,698,090 A | 10/1987 | Marihart |
| 4,769,221 A | 9/1988 | Marihart |
| 4,786,307 A | 11/1988 | Marihart |
| 5,514,200 A | 5/1996 | Lovatt |
| 5,830,255 A | 11/1998 | Lovatt |
| 6,080,220 A | 6/2000 | Sequi et al. |
| 6,113,665 A | 9/2000 | Lovatt |
| 6,277,847 B1 * | 8/2001 | Theodoridis et al. ....... 504/242 |
| 6,338,860 B1 | 1/2002 | Taylor |
| 2002/0048609 A1 | 4/2002 | Taylor |

OTHER PUBLICATIONS

Merriam Webster's Collegiate Dictionary, 10$^{th}$ edition, 1996, pp. 564–565.*
Almond Board of California, "Years of Discovery," 1998, pp. 16,20–22,33–35,49–50,171–172.
Almond Board of California, "Ready, AIM, Fire," 1999, pp. 41–43.
Almond Board of California, "50 Years of Progress," 2000, pp. 47–53.
Almond Board of California, "29th Annual Almond Industry Conference," 2001, pp. 65–71.

* cited by examiner

*Primary Examiner*—Alton Pryor
*Assistant Examiner*—Rozenia Harmon
(74) *Attorney, Agent, or Firm*—Roth & Goldman, P.A.

(57) ABSTRACT

A fungicidal composition for controlling fungal diseases in plants, which includes a fungicide, and a complex organic composition derived from natural organic materials. The organic composition may comprise a humic acid composition, a fulvic acid composition, a humin component composition, mixtures thereof or other extracts from natural organic materials such as leonardite, lignite, peat, shale, sediments and soil. The fungicidal composition includes a phosphorus-containing compound such as phosphorous acid, a phosphite salt, and a phosphate salt or mixtures thereof. The preferred embodiments of the compositions provide enhanced control of select fungal diseases in plants as well as enhanced plant nutrient uptake abilities. The invention also includes processes for producing the fungicidal compositions and methods for applying the fungicidal compositions to plants.

26 Claims, 1 Drawing Sheet

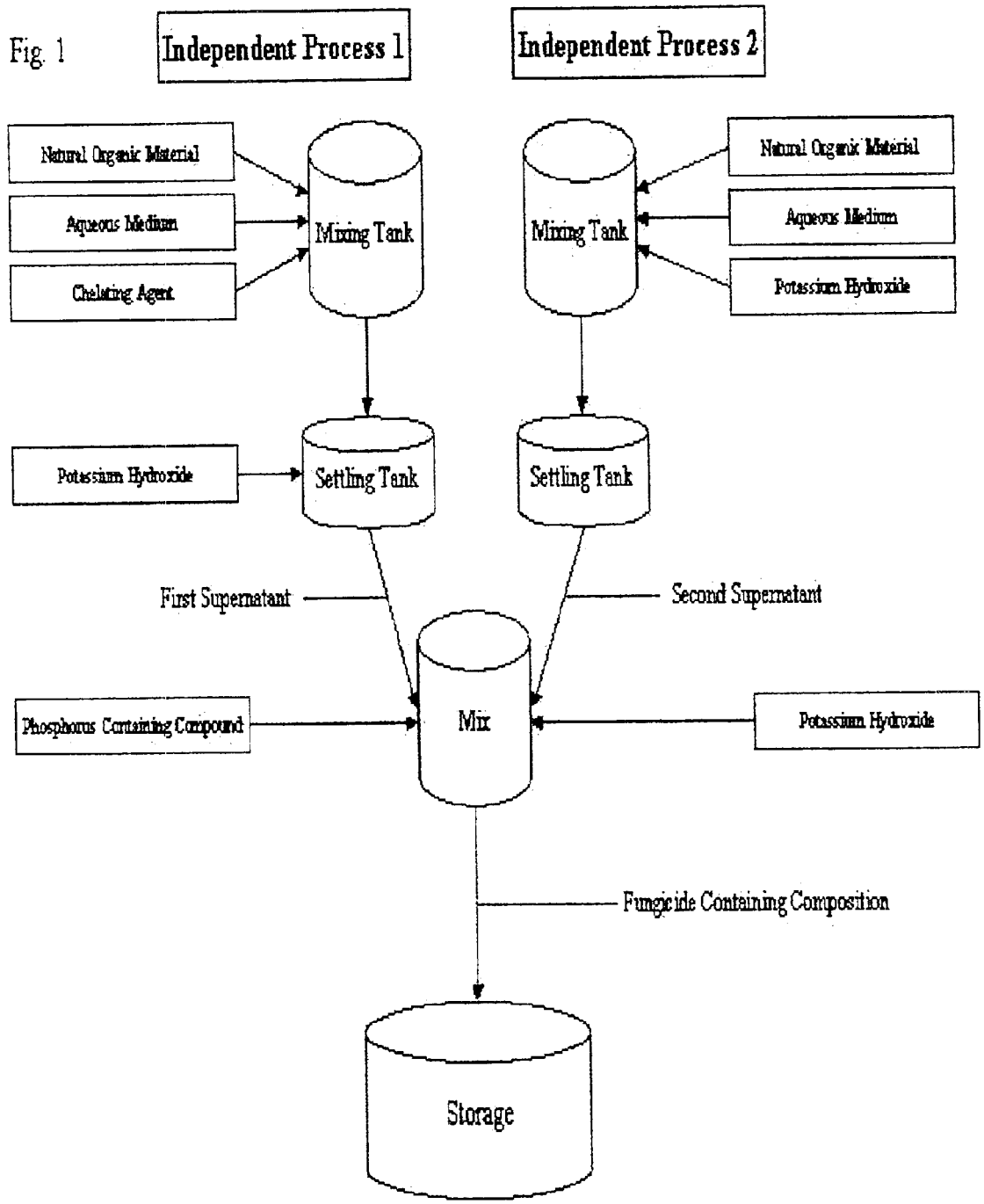

FUNGICIDAL COMPOSITIONS CONTAINING ORGANIC COMPOSITIONS DERIVED FROM NATURAL ORGANIC MATERIALS, PHOSPHOROUS ACID, PHOSPHITE SALTS AND PHOSPHATE SALTS, METHODS OF MAKING SAME AND METHODS OF APPLYING SAME TO PLANTS

CROSS REFERENCE TO RELATED APPLICATIONS

This application claims the priority of prior provisional application by Carl Ueland, Ser. No. 60/296,928 filed Jun. 9, 2001.

FIELD OF THE INVENTION

This invention relates to fungicides for controlling plant diseases. More specifically this invention pertains to fungicidal compositions based on a complex mixt5ure of organic substances extracted from natural organic materials such as leonardite, lignite, peat, shale, sediments and soil in association with phosphorous acid, a phosphite salt and/or a phosphate salt. Some of the compositions of the present inventions also have fertilizer properties. The invention includes fungicidal compositions, methods of making the fungicidal compositions, and methods of applying such compositions to plants and to soil.

BACKGROUND OF THE INVENTION

The present invention relates to fungicidal compositions, methods of making the compositions and methods of applying such compositions to control fungal diseases of plants. Phosphorus containing compounds with fungicidal properties and fertilizer capabilities have already been proposed as disclosed in the prior patents detailed herein. None of these patents however, include as an active ingredient, a complex organic composition derived from natural organic materials such as leonardite, lignite, peat, shale, sediments and soil. Such organic compositions are believed to enhance the effectiveness of the phosphorus containing compounds in controlling fungal diseases.

Standard fertilizers generally comprise blends of one or more nitrogen containing compounds (e.g. nitrate or ammonium salts), a phosphorus containing compound (e.g. phosphate), and potassium. Such fertilizers are generally not used for their fungicidal effect. These fertilizers have been combined with liquid plant growth modification compositions of the type described in U.S. Pat. No. 4,698,090 issued to Marihart and/or with liquid plant growth compositions of the type described in U.S. Pat. No. 4,786,307 issued to Marihart. The U.S. Pat. No. 4,698,090 discloses a process for extraction of humic acids by reacting organic chelating agents with leonardite ore, and U.S. Pat. No. 4,786,307 discloses methods of preparing chelated micronutrient compositions containing fulvic acid substantially free of humic acid and extracted from leonardite ore with a chelant. These extracts from leonardite ore are complex compositions containing thousands of interactive compounds, the beneficial effects and properties of which are not fully understood.

Nutritional functions of humic substances are described in U.S. Pat. No. 6,080,220 issued to Sequi, et al. That patent discloses that the nutritional functions of humic substances are both direct, when the nutritive elements are released in the course of slow mineralization of humic substances themselves, and indirect, when their ability to complex and chelate the metals that are found in the liquid phase allow for plant uptake of the nutrients. In nature the indirect nutritional function is considered the more important one for making available different nutritional metals, such as iron, calcium, and magnesium. Humic substances tend to chelate the metals present in the soil solution, thus preventing the precipitation of the metals in the forms of oxides, hydroxides or carbonates, which then become unusable because they are in insoluble forms that cannot be absorbed by the root hairs of plants. Chelation by the humic substances makes the metals available for nutritional purposes.

U.S. Pat. No. 5,830,255 issued to Lovatt and U.S. Pat. No. 6,113,665 issued to Lovatt, disclose concentrated water dilution fertilizers comprising buffered compositions of a phosphorus containing acid or salt thereof which, when diluted with water, have a foliage acceptable pH for phosphorus uptake as a fertilizer.

Compositions for control of fungus are known including, for example, the fungicidal compositions containing phosphorous acid disclosed in U.S. Pat. No. 4,075,324 issued to Thizy and the commercial ALIETTE® WDG composition containing aluminum tris (O-ethyl phosphonate) as active ingredient from Aventis Crop Science which is foliarly applied for control of Downy Mildew in lettuce crops. Another example of a composition for the control of fungus is the use of phosphate and phosphonate disclosed in U.S. Pat. No. 6,338,860 issued to Taylor and the commercial PHOS-MIGHT composition from Foliar Nutrients, Incorporated for control of *Phytophthora* infection in plants. More effective fungicidal compositions are desired, particularly those, which are also capable of stimulating and enhancing plant growth, and have little effect on the environment.

Historically, application of fungicidal materials has been predominantly limited to foliar applications. Since the mode of action of most of these materials has been of a contact nature, direct contact of the fungicide with the disease organism has been one the limiting factors impacting the efficacy of many fungicides. Applications of the materials directly to the plant foliage have been the most widespread methods of delivery. This direct application method is inherently expensive as it requires foliar application apparatus and labor to apply these materials. Further reductions in efficacy are attributed to "washing-off" by rain or sprinklers which removes the fungicide from its intended location of placement. More recently newer fungicide chemistries have allowed for application of these fungicides to the soil. Applications of phosphorus fungicide materials directly to the soil are subject to chemical "tie-up" and have been limited in their effectiveness under soil conditions.

SUMMARY OF THE INVENTION

Fungi and fungal deceases have always been a major hindrance to crop production and ornamentals. It is an object of the present invention to provide a unique fungicide for use in agriculture, forestry, and horticulture that is more efficacious on a variety of fungal diseases that attack plants.

It has now been discovered that significantly improved fungicidal control can be obtained by applying commercial fungicidal compositions containing active ingredients such as aluminum tris (O-ethyl phosphonate), phosphate salt, phosphorous acid, iprodione, in combination with natural organic material such as leonardite extract compositions of the types disclosed in the above Marihart patents. The combination of fungicidal compositions and natural organic materials more effectively alleviates fungal disease, such as Downy Mildew on lettuce and onions, and is effective in the control of *Phytophthora* root rot in young almond trees, as will be described.

The compositions of the present invention comprise, as active ingredients, a fungicide, at least one organic composition derived from natural organic material such as leonardite, lignite, peat, shale, sediments and soil, and, preferably, at least one of phosphorous acid, a phosphite salt and a phosphate salt, iprodione: 3-(3,5-dichlorophenyl)-N-(1-methylethyl)-2,4-dioxo-1-imidazolidinecarboxamide and aluminum tris (O-phosphonate).

The fungicidal compositions disclosed herein therefore contain, as an active ingredient, at least one compound which, when applied to the plant provides phosphorus thereto in an amount and form effective for controlling fungal diseases and, preferably, at least one compound which, when applied to the plant, provides phosphate thereto in an amount effective for increasing plant growth.

Examples of fungicides containing phosphorous acid and its salts suitable for controlling fungal disease in accordance with the present invention include the alkali inorganic salts of potassium; organic salts of humates and compounds which can accept a proton from phosphorus acid, such as primary, secondary or tertiary amines.

The present invention, a fungicide solution of organic compositions derived from natural organic materials combined with phosphorous acid and its derivatives, greatly reduces infestation by a variety of fungi including *Phytophthora* and Downy Mildew. Improved results have been found when the invention has been applied to a plant both as a foliar application and applied directly to the soil.

The composition is a dark liquid concentrate, which can be diluted with water of pH ranging from about 6 to about 8, at ratios of concentrate to water from about 1:10 to about 1:400 on a weight/weight basis. The result of such dilution is a safe fungicide that is readily absorbed by a plant with no toxicity to the plant.

Three independent methods and their basic procedures for making the improved fungicide are included. They include, directions on how to prepare the different organic compositions derived from natural organic materials and specify the order, timing and controls in mixing these compositions with phosphorus containing compounds. Also included is a flow chart of the processes for clarity.

Procedures for applying the invention as a fungicide to plants are included. Such procedures include diluting a concentrate comprised of organic compositions derived from natural organic materials with phosphorus containing compositions and their derivatives with water to form an aqueous solution having a pH range acceptable for plant absorption. Foliar application, irrigation system application, soil application and dry applications are included.

Definitions of specific terms used herein are as follows:
Definitions of Terms

The following terms are defined to improve clarity and understanding, and are not meant to be limiting in any way. Various terms, shown in italics when first used below, are defined here insofar as these terms are used throughout the body of the specification and in the claims of this patent.

The term *chelating agent* is used to describe certain organic chemicals that form ring compounds in which a polyvalent metal is held between two or more atoms.

The term *fertilizer grade (N-P-K)* is an expression indicating the weight percentage of plant nutrients in a fertilizer. The expression is stated in terms of the percentages of nitrogen (N), phosphate ($P_2O_3$), and potash ($K_2O$), in that order.

The term *humic substances* is a general category of naturally-occurring, biogenic, heterogeneous organic substances that is used to describe a complex mixture of organic materials that are extracted from natural substances such as leonardite, lignite, peat, shale and soil as well as from natural waters. Humic substances originate from the decay of plant and microbial residues in the environment. Humic substances are generally classified into three fractions based on the treatment of the substrate with alkali, typically a solution of sodium hydroxide or potassium hydroxide, or a solution of an alkali metal salt of a chelating agent. Humic substances have aromatic and aliphatic portions and they contain an abundance of carboxyl, alcohol and phenolic functional groups, as well as other functional groups. These substances have acidic, complexing and redox properties, and can exhibit both hydrophilic and hydrophobic properties depending on the circumstances. Because of these features the humic substances can interact with and bind to many species including metal ions, mineral and oxide surfaces, and organic chemicals such as pesticides.

The term *fulvic acid* is operationally defined as the fraction of humic substances that is soluble in water under all pH conditions.

The term *humic acid* is operationally defined as the fraction of humic substances that is not soluble in water under acid conditions, but becomes soluble at greater pH.

The term *humin* is defined operationally as the fraction of humic substances that is not soluble in water at any pH.

The term *leonardite* is generally considered to be an oxidized form of lignite coal. Leonardite is generally found in the overburden covering lignite coal deposits. It is more oxidized than the underlying lignite and is generally unsuitable for use as a fuel. Leonardites generally have a high content of humic acids. Leonardite is sometimes simply referred to as lignite.

The term *natural organic materials* in the context of this specification, including the claims, refer to naturally occurring organic matter found in such natural substrates as leonardite ore, lignite, peat, sediments, shale and soil. The term natural organic materials in the context of the specification and claims also includes those components in the extracts from leonardite, lignite, peat, sediments, shale, and soil that may have undergone chemical alteration or degradation during extraction. Such natural organic materials typically include fulvic acids, humic acids and humin, chemically altered or degraded variants thereof as well as other organic substances.

The term *peat* refers to partially decayed vegetable matter of natural occurrence that is composed chiefly of organic matter than contains some nitrogen of low activity.

The trademark Aliette® owned by Aventis Crop Science refers to a fungicide containing composition with its active ingredient, aluminum tris (O-ethyl phosphonate). This fungicide is also commonly referred to as fosetyl-al or fosetyl-aluminum.

The trademark Monarch® is owned by Actagro, LLC and refers to a fertilizer composition containing 2-20-15 primary plant nutrients with 3% non plant food organic compositions derived from natural organic materials.

The trademark Resist is used by Actagro, LLC and refers to a fungicide containing composition with its active ingredient, phosphorous acid, and also containing 0-21-18 primary plant nutrients and 2.5% non-plant food organic compositions derived from natural organic materials.

The trademark Rovral® owned by Aventis Crop science refers to a fungicide containing composition with its active ingredient, iprodione.

In the claims of this invention, all concentrations are expressed on a weight/weight percent basis, meaning the weight of a constituent divided by total weight of sample, multiplied by 100.

In some stages in the processes of the present invention, mixtures are allowed to sit and suspensions are allowed to settle, at least in part. The term supernatant means the liquid phase containing dissolved and suspended material. The term settled sludge refers to the solid matter that settles to the bottom of the container and that remains behind when the supernatant is removed.

A fungicide that can be applied at small rates and that is largely composed of ingredients that are relatively safe to the environment will be disclosed. The composition generally comprises organic compositions derived from natural organic materials and phosphorous acid and its derivatives in a stable fungicide formulation devoid of settled percipitates. The composition may contain both a fungicide and a nutrient to a plant. An organic composition derived from natural organic materials blended in a singular plant nutrient formula, such as: nitrogen, phosphate and potassium may then be combined with another phosphorus containing fungicide to greatly improve the efficacy for reducing Downy Mildew on a plant. Commercially available phosphorous acid and phosphoric acid products can be used as starting material and neutralized to produce other salts by conventional processes.

BRIEF DESCRIPTION OF THE DRAWING

FIG. 1 comprises a flowchart, which shows the basic steps involved in producing compositions of the present invention.

DETAILED DESCRIPTION OF THE PREFERRED EMBODIMENT

A variety of organic compositions and derivatives can be obtained by the reaction of organic chelating agents with natural organic materials such as leonardite, lignite and peat, as more fully described in the above Marihart patents, the disclosures of which are fully incorporated herein by reference. Preferably, leonardite ore having a relatively high humic substance content, such as that commonly mined in North Dakota, having an organic matter content as high as 80% by weight, is used. Leonardite ore, preferably crushed prior to the use thereof, is reacted in a heated aqueous medium in the presence of one or more organic chelating agents under alkaline conditions. Preferably the aqueous medium is heated prior to the introduction of the reactants.

Representative of the organic chelating agents adapted for use in carrying out the process are the following:

(1) Gluconic acid, glucoheptonic acid, citric acid, tartaric acid, tartronic acid, galactaric acid, glucaric acid, glutaric acid, and glutamic acid, and the ammonium salts and metal salts thereof, such metal salts including the sodium, potassium, copper, iron, magnesium, manganese, zinc, calcium, lithium, rubidium and cesium salts of such acids;

(2) Sodium glucamine, potassium glucamine, ammonium glucamine, copper glucamine, ferrous glucamine, magnesium glucamine, manganese glucamine, zinc glucamine, calcium glucamine, lithium glucamine, rubidium glucamine, and cesium glucamine; and (3) Materials commonly referred to as "synthetic" organic chelating agents, and more particularly the group consisting of amino acid chelating agents representative of which are ethylene-diaminetetraacetic acid (EDTA), hydroxyethylenediaminetriacetic acid (HEDTA), diethylene-triaminepentaacetic acid (DTPA), nitrilotriacetic acid (NTA), ethylenediamine di (ortho-hydroxyphenylacetic acid) (EDDHA), and ethanol diglycine, as well as the ammonium salts and metal salts thereof, most particularly the sodium salts, and monoethanolamine (MEA).

Preferably, although not necessarily, the organic chelating agent or agents chosen are water-soluble. In a modified form of the process the pH of the resultant aqueous organic compositions is then adjusted to stabilize the composition against oxidation and degradation, and to provide a prolonged potential shelf life. In a further modified form of the process, the composition derived by the reaction of leonardite ore with one or more organic chelating agents is blended with an organic composition prepared by the reaction of leonardite ore with potassium hydroxide, sodium hydroxide or ammonium hydroxide.

The organic compositions previously described are mixed with a base selected such as ammonium hydroxide, potassium hydroxide or sodium hydroxide to create an alkaline solution to be reacted with a phosphorus containing composition such as phosphorous acid and phosphoric acid. As the premix of organic compositions and a base are reacted with the phosphorus containing composition, the resulting reaction is temperature controlled between 100° F. and 200° F. pH is maintained between about pH 2 and about pH 7, until the proper amount of phosphorus containing compounds is in solution and reacted.

The flowchart of FIG. 1 is included as an aid to understanding the process of this invention for producing the fungicidal compositions and is not intended to be limiting. In the flowchart of FIG. 1 cylinders represent mixing tanks, settling tanks, holding tanks and storage tanks. The lines emanating from the bottom of these tanks depict the transfer of material from the respective tank into the tank at which the arrows are pointing. The complete contents of each tank are transferred to the next tank except in those cases where the word first or second "supernatant" appears beside the arrow. In these cases only the supernatant is transferred to the next tank. The horizontal arrows indicate the addition of materials into the corresponding tanks.

The following procedures are used to make organic compositions derived from natural organic material. Nine parts by weight of natural organic materials, preferably leonardite, are mixed into seventy-five parts by weight of an aqueous medium, preferably water, which has been previously heated, preferably, to a temperature in a range of from about 190° F., but not exceeding 225° F. Next, fifteen parts by weight of a complexing agent, preferably sodium gluconate, the sodium salt of gluconic acid, is added and the resultant composition is mixed for approximately five hours to permit complete reaction. After mixing, the mixture is pumped into a settling tank and allowed to settle for at least twenty-four hours, but preferably allowed to settle for seven days in order to separate into a supernatant and a settled sludge, after which the supernatant is pumped to standard cone tanks and allowed to settle for an additional two to three days. The resultant second supernatant is pumped to a mixer and adjusted therein to a pH of 12.5 or higher by the addition of concentrated sodium hydroxide or potassium hydroxide. This final liquid composition will be referred to as "First supernatant".

Independently, seventy-two parts by weight of an aqueous medium, preferably water, is heated to at least 180° F., but preferably to about 200° F. About twenty parts by weight of a natural organic material, preferably leonardite, is added to the heated water and mixed for about one-half hour. Next, five parts by weight of potassium hydroxide or sodium hydroxide is added to the solution to raise the pH to about 11, and mixed for a period of about two hours. Thereafter, one part by weight of hydrogen peroxide is added. The resultant liquid composition is permitted to settle, and the supernatant is removed and will be referred to as "Second supernatant".

Next, about eighteen parts by weight of Second supernatant is added to about four parts by weight of First supernatant and mixed for about one hour. To the resulting composition, about sixty parts by weight of potassium hydroxide is added and mixed for approximately 1 hour. Next, five parts by weight of a phosphorus containing compound, preferably phosphorous acid, are pumped into a mixing tank. The reactant temperature is controlled by the rate of flow and amount of phosphorous acid being added and is maintained at approximately between 100° and 200° F., preferably at about 140° F. The pH of the reactant is also controlled in a range between pH 2 and pH 7, preferably at about pH 4.5. The resultant fungicidal composition is the pumped into storage.

In order to disclose the uses of the subject invention still more clearly, attention is invited to the following illustrative examples. It is understood, however, that these examples are merely illustrative and that the subject invention is not to be limited to the specific conditions or details set forth. The fungicidal properties of the compounds according to the invention are various, but are particularly interesting in the case of Downey Mildew, *Phytophthora* root rot, and Leaf Shot Hole.

EXAMPLE 1

Head Lettuce (*Lactuca sativa* var. Cowboy) was allowed to develop the disease Downy Mildew (infested with the pathogenic fungus *Bremia lactucae*) to determine if a treatment of a liquid plant nutrient composition Monarch® fertilizer, a compound containing 2-20-15 primary plant nutrients and 3% non-plant food organic compositions derived from natural organic materials, would increase the efficacy of Aliette® 80 WDG (fosetyl-aluminum) fungicide. Downy Mildew symptoms on lettuce leaves may not show until five to ten days after initial infection period. Devastating crop loss can result from this disease, which can spread rapidly, completely enveloping all exposed leaves.

An independent trial was conducted comparing an untreated check and four different treatment combinations and each replicated four times. The foliar applications were made four times to each replicate in combination with 30 gallons of water per acre. Applications were made on a seven-day schedule. An evaluation for mildew incidence and severity was done prior to the third application and a second evaluation was conducted seven days after the last application.

The results are shown in Table 1:

TABLE 1

Summary Downy Mildew Efficacy Field Trial: Head Lettuce

| | | First Evaluation | | Second Evaluation | |
| --- | --- | --- | --- | --- | --- |
| Treatment | Rate Per Acre | Column 1 Average # infected/ 5 plants | Column 2 Average % infected/ 5 plants | Column 3 Average # infected/ 5 plants | Column 4 Average % infected/ 5 plants |
| Aliette 80 WDG Potassium Carbonate | 3.2 lb 1.8 lb | 4.5 | 7.55 | 4.0 | 6.00 |
| Aliette 80 WDG Potassium Carbonate Monarch 2-20-15 | 3.2 lb 1.8 lb 1.0 pt | 3.3 | 2.70 | 3.5 | 2.55 |
| Aliette 80 WDG Potassium Carbonate Monarch 2-20-15 | 3.2 lb 1.8 lb 2.0 pt | 3.0 | 2.45 | 3.8 | 2.45 |
| Untreated Check | — | 4.8 | 13.40 | 5.0 | 19.20 |

The first evaluation shows in Column 1, the average number of infected plants ranging from a high of 4.8 with the untreated check to a low of 3.0 with the Aliette® fungicide/Monarch® fertilizer combination. While the average numbers vary, they are not considered statistically different. Column 2 shows that superior control as measured by severity of infection (Average % infected) ranging from 13.40% for the untreated check to 7.55% with Aliette® fungicide alone, and with a low of 2.45% with the Aliette® fungicide/Monarch® fertilizer combination. The second evaluation shows in Column 3 all treated rows having superior mildew control (# infected) when compared to the untreated check. Column 4 shows superior control as measured by severity (% infected), ranging from 6.0% with the Aliette® fungicide alone, to a low of 2.45% with the Aliette® fungicide/Monarch® fertilizer combination. Clearly, combination treatments of Aliette® fungicide plus Monarch® fertilizer provided superior control of Downy Mildew over the untreated check and over Aliette® fungicide, alone.

EXAMPLE 2

Head Lettuce (*Lactuca sativa* var. Desert Storm M 1 Maxi) was allowed to develop the disease Downy Mildew (*Bremia lactucae*) to determine if treatment by a liquid organic phosphorus composition containing 0-21-18 primary plant nutrients and 2.5% non-plant food organic compositions derived from natural organic materials (i.e., the RESIST composition) would provide effective control of Downy Mildew in head lettuce. The test also allows a comparison of RESIST fungicide alone versus Aliette® 80 WDG (fosetyl-aluminum) fungicide in controlling Downy Mildew symptoms on lettuce leaves.

An independent trial was conducted comparing an untreated check and three treatment combinations each replicated four times. Foliar applications of treatment materials in combination with 30 gallons per acre of water were made two times to each replicate. The first applications were made prior to disease appearance and the second applications were made ten to fourteen days after the first application. Evaluations for mildew incidence and severity were made ten days after the first application, and the second evaluation six to ten days after the last application.

The results are shown in Table 2:

TABLE 2

Summary Downy Mildew Efficacy Field Trial: Head Lettuce

| | | First Evaluation | | Second Evaluation | |
| --- | --- | --- | --- | --- | --- |
| Treatment | Rate Per Acre | Column 1 Average # infected/ 5 plants | Column 2 Average % infected/ 5 plants | Column 3 Average # infected/ 5 plants | Column 4 Average % infected/ 5 plants |
| RESIST (Organo Phite) | 1 qt | 1.3 | 1.50 | 2.0 | 3.35 |
| RESIST | 2 qt | 1.5 | 2.00 | 1.8 | 2.65 |
| Aliette ® | 4.0 lb | 1.5 | 2.30 | 1.8 | 3.05 |
| Untreated Check | | 2.3 | 2.95 | 3.8 | 7.60 |

The first evaluation shows in Columns 1 and 2, an improvement in control of incidence and severity with RESIST fungicide and Aliette® fungicide each compared to the untreated check. However, these results were not statistically different. The second evaluation shows in Columns 3 and 4, that treatments of RESIST fungicide and Aliette® fungicide provide superior control of Downy Mildew compared to the untreated check. RESIST fungicide was equally as effective as Aliette® 80 WDG fungicide in controlling Downy Mildew in head lettuce.

EXAMPLE 3

Fresh Market Onions (*Allium cepa* var. Early Supreme) were allowed to develop the disease Downy Mildew (*Peronospora destructor*). In this example, the onions were separately treated with Aliette® fungicide, RESIST fungicide, and with a combination of RESIST fungicide/ Monarch® fertilizer to determine if treatment with RESIST fungicide, or a combination of RESIST fungicide/ Monarch® fertilizer would provide effective control of Downy Mildew symptoms on onion leaves versus Aliette® 80 WDG (fosetyl-aluminum) fungicide.

An independent trial was conducted comparing an untreated check and four treatment combinations each replicated four times. Foliar applications of treatment materials in combination with 30 gallons of water per acre were made two times to each replicate.

The first application was made after the first sign of disease appearance with the second application being made seven days after the first application. Evaluations for mildew incidence and severity were conducted at random. The results are shown in Table 3:

TABLE 3

Summary Downy Mildew Efficacy Field Trial: Onions

| | | First Evaluation | | Second Evaluation | |
| --- | --- | --- | --- | --- | --- |
| Treatment | Rate Per Acre | Column 1 Average # infected leaves/ 10 plants | Column 2 Average % infected leaves/ 10 plants | Column 3 Average # infected leaves/ 10 plants | Column 4 Average % infected leaves/ 10 plants |
| Untreated Check | — | 8.5 | 10.75 | 9.5 | 25.40 |
| Resist | 1.0 qt | 3.5 | 0.83 | 6.0 | 3.88 |
| Resist | 2.0 qt | 5.8 | 3.95 | 8.0 | 13.60 |
| Resist | qt | 5.8 | 3.05 | 7.8 | 9.85 |
| Monarch ® Aliette ® Potassium Carbonate | qt 3.0 lb 1.8 lb | 4.3 | 1.38 | 7.3 | 6.78 |

The first evaluation shows in Columns 1 and 2 for incidence of infected leaves that RESIST fungicide at one quart per acre provides control superior to the standard Aliette® fungicide treatment and untreated check. For a severity rating, Columns 2 and 4, show all treatments were superior to the untreated check, but with no statistical separation between treatments. Columns 3 and 4, also show RESIST fungicide at two quarts per acre and RESIST fungicide at one quart per acre in combination with Monarch® fertilizer provides superior control compared to the untreated check but slightly less than Aliette® fungicide.

This trial demonstrates that RESIST fungicide effectively controlled Downy Mildew in Onions, that RESIST fungicide provided effective control, which was superior to control of Downy Mildew in Onions as compared to Aliette® fungicide, and that RESIST fungicide plus Monarch® fertilizer provided control which was equally as effective in controlling Downy Mildew in Onions as Aliette® fungicide.

EXAMPLE 4

Almond Trees (*Prunus dulcis* var. nonpareil) were allowed to develop the disease Leaf Shot Hole (infested with the pathogenic fungus *Stigmina carpophila*, aka. *Wilsonmyces carpophilus*) to determine if treatment by Monarch® fertilizer would increase the efficacy of Rovral® (Iprodione) fungicide in controlling this disease. Leaf Shot Hole spores over winter on living twigs and buds as well as leaves and nuts. Spores produced in the fall germinate in ten to sixteen hours in early spring under optimal conditions of temperature and moisture producing *sporodochia* fruiting structures. These *sporodochia* structures produce necrotic lesions which "fall-out" producing the "shot hole effect." This disease can spread rapidly in almond orchards infesting not only leaves, twigs, and buds, but can infest almond fruit directly causing the fruit to abort (drop). Through drop and loss of tree vigor, total yield can be severely impacted by as much as fifty to seventy percent. Dormant fungicide treatments have proven to be ineffective in controlling this disease and only moderate suppression of the spore germination has been documented by fungicides used in dormant sprays.

An independent trial was conducted comparing an untreated check and two treatment combinations replicated four times on four trees in each replication. Foliar applications were made two times to each replicate. Foliar applications were made at pink bud (early spring) and at full bloom (one week later). Evaluations for shot hole incidence (percent infected leaves) were made by selecting at random ten shoots and observing ten leaves on each shoot. Shot hole evaluation on nuts was done by selecting fifty nuts per tree and observing them for any shot hole infection. This data was recorded as percent infected nuts. Trial was evaluated eleven days after treatment at full bloom.

The results are shown in Table 4:

TABLE 4

Summary Leaf Shot Hole Efficacy Field Trial: Almonds

| Treatment | Rates per acre | Column 1 % infected leaves | Column 2 % infected nuts |
|---|---|---|---|
| Monarch ® | 1 gal | 1.8 | 0.0 |
| Rovral ® | 1.0 pt | | |
| Rovral ® | 1.0 pt | 3.0 | 1.5 |
| Untreated Check | | 4.5 | 5.0 |

Treatments of Monarch® fertilizer in combination with Rovral® fungicide, as shown is Columns 1 and 2, provided superior control of Leaf Shot Hole in terms of incidence of infection on leaves and nuts. Rovral® fungicide, as shown in Columns 1 and 2, provided only intermediate numerical control compared to the untreated check. Monarch® fertilizer in combination with Rovral® fungicide enhanced the efficacy of Rovral® fungicide in controlling Leaf Shot Hole.

EXAMPLE 5

In-vitro treatment of *Phytophthora cactorum* (a pathogenic fungus) with a liquid organic phosphorous acid containing composition RESIST (composition containing 0-21-18 primary plant nutrients and 2.5% non-plant food organic compositions derived from natural organic deposits) fungicide was conducted to determine if said composition is directly phytotoxic to this disease organism. Aliette® 80 WDG (fosetyl-aluminum) fungicide was included as a comparison product due to its current use in controlling this disease organism under field conditions.

A culture of *Phytophthora cactorum* was established on V-8 agar media. Inoculum of the fungus was prepared by blending contents of one culture plate, containing mycelium and sporangia, in distilled water. The inoculum was mixed with five separate dilutions with sterilized extracts of RESIST fungicide and incubated for one hour. After incubation, ten samples were each assayed on PAR media and *Phytophthora* colonies evaluated and counted one week later. Two dilutions of Aliette® 80 WDG fungicide were prepared in the same manner as well as an untreated check. All dilutions and the untreated check were replicated three times. The results are shown in Table 5:

TABLE 5

Summary of *Phytophthora cactorum* Efficacy In-vitro Trial

| | | # *Phytophthora* colonies recovered | | | |
|---|---|---|---|---|---|
| Treatment | Concentration % | Rep 1 | Rep 2 | Rep 3 | Mean |
| Untreated Check | | 2 | 2 | 3 | 2.33 |
| RESIST | 1% | 1 | 2 | 2 | 1.66 |
| RESIST | 10% | 0 | 0 | 0 | 0 |
| RESIST | 25% | 0 | 0 | 0 | 0 |
| RESIST | 50% | 0 | 0 | 0 | 0 |
| RESIST | 100% | 0 | 0 | 0 | 0 |
| Aliette ® 80 WDG | 10% | 2 | 3 | 1 | 2.00 |
| Aliette ® 80 WDG | 1% | 2 | 4 | 2 | 2.66 |

Treatments as shown in Columns Rep 1 through Rep 3 demonstrate that RESIST fungicide at concentrations of ten percent and higher is effective at controlling *Phytophthora*. Aliette® fungicide appeared to be ineffective in controlling *Phytophthora* at either concentration in this trial. As represented by no colonies recovered, Columns Rep 1 through Rep 3, RESIST fungicide is phytotoxic to *Phytophthora cactorum* at concentrations above ten percent.

The present invention is presented and described in what are considered to be the most practical and preferred embodiments. It is recognized, however, that departures may be made there from which are within the scope of this invention, and that obvious modifications will occur to one skilled in the are upon reading this disclosure.

We claim:

1. A composition for controlling fungal diseases in plants, consisting essentially of
   a) a fungicide comprising a phosphorous containing compound selected from the group consisting of phosphorous acid, phosphite salts and phosphate salts and mixtures thereof; and
   b) at least one component selected from the group consisting of humic acid, fulvic acid, and humin present in an effective amount up to 30% by weight derived by chemical extraction from at least one of the group consisting of leonardite, lignite, peat, shale, sediments and soil
   c) and optionally phosphoric acid and optionally 3-(3,5-dichlorophenyl)N(1-methylethyl)-2,4-dioxo-1-imidazolidine carboxamide.

2. The composition of claim 1, wherein component b) of claim 1 is a humic acid.

3. The composition of claim 1, wherein component b) of claim 1 is a fulvic acid.

4. The composition of claim 1, wherein component b) of claim 1 is a humin.

5. The composition of claim 1, wherein component b) of claim 1 is a mixture of humic acid and fulvic acid.

6. The composition of claim 1, wherein component b) of claim 1 is a mixture of humic acid and a humin.

7. The composition of claim 1, wherein said component b) of claim 1 is a mixture of fulvic acid and a humin.

8. The composition of claim 1, wherein component b) of claim 1 is a mixture of humic acid, fulvic acid and a humin.

9. The composition of claim 1, wherein said phosphorus containing compound comprises phosphorous acid.

10. The composition of claim 1, wherein said phosphorus containing compound comprises a phosphite salt.

11. The composition of claim 1, wherein said phosphorus containing compound comprises a phosphate salt.

12. The composition of claim 1, wherein phosphoric acid is present.

13. The composition of claim 1, wherein comprises 3-(3, 5-dichlorophenyl)-N-(1-methylethyl)-2, 4-dioxo-1-imidazolidine-carboxamide is present.

14. The composition of claim 13, wherein phosphoric acid is present.

15. The composition of claim 13, wherein phosphate salt is present.

16. The composition of claim 1, wherein is aluminum tris (O-ethyl phosphonate) is present.

17. The composition of claim 1, in a dry form wherein said component b) is present in an effective amount of from about 1% to about 30% on a weight/weight basis.

18. The composition of claim 1, further comprising water and wherein said component b) is present in an effective amount of from about 0.05% to about 12% on a weight/weight basis.

19. A method of applying a composition as defined in claim 1 as a dry formulation comprising the steps:

a) adding said composition to an aqueous medium to produce an aqueous mixture;

b) applying said aqueous mixture onto a carrier selected from the group consisting of a dry fertilizer material and a dry substrate material to produce a dry fungicide-plus-carrier combination; and c) applying said dry fungicide-plus-carrier combination to soil to control fungal diseases in plants.

20. A method of applying a composition as defined in claim 1 as a liquid formulation comprising the steps:

a) adding said composition to an aqueous medium to produce an aqueous mixture;

b) applying said aqueous mixture onto a carrier selected from the group consisting of a dry fertilizer material and a dry substrate material to produce a dry fungicide-plus-carrier combination; and c) applying said dry fungicide-plus-carrier combination to soil to control fungal diseases in plants.

21. A method of applying a composition as defined in claim 1 as a dry formulation comprising the steps:

a) adding said composition to an aqueous medium to produce an aqueous mixture;

b) mixing thoroughly in a vessel; and c) applying said aqueous mixture to the soil to control fungal diseases in plants.

22. A method of applying a composition as defined in claim 1 as a liquid formulation comprising the steps:

a) adding said composition to an aqueous medium to produce an aqueous mixture;

b) applying said aqueous mixture to the soil to control fungal diseases in plants.

23. A method of applying a composition as defined in claim 1 as a dry formulation comprising the steps:

a) adding said composition to an aqueous medium to produce an aqueous mixture; and b) applying said aqueous mixture directly to plant foliage, twigs, stems, and bark to control fungal diseases in plants.

24. A method of applying a composition as defined in claim 1 as a liquid formulation comprising the steps:

a) adding said composition to an aqueous medium to produce an aqueous mixture; and b) applying said aqueous mixture directly to plant foliage, twigs, stems, and bark to control fungal diseases in plants.

25. A method of applying a composition as defined in claim 1 as a liquid formulation comprising the steps:

a) adding said composition to an aqueous medium to produce an aqueous mixture; and b) applying said aqueous mixture to soil by means of introduction into a water distribution system to control fungal diseases in plants.

26. A method of applying a composition as defined in claim 1 as a dry formulation comprising the steps:

a) adding said composition to an aqueous medium to produce an aqueous mixture; and b) applying said aqueous mixture to soil by means of introduction into a water distribution system to control fungal diseases in plants.

\* \* \* \* \*